US012735690B2

(12) United States Patent
Otsushi

(10) Patent No.: US 12,735,690 B2
(45) Date of Patent: Sep. 15, 2026

(54) COMPOSITION FOR IMPROVING UNPLEASANT TASTE CAUSED BY HIGH-INTENSITY SWEETENER

(71) Applicants: ASAHI GROUP FOODS, LTD., Tokyo (JP); ASAHI GROUP HOLDINGS, LTD., Tokyo (JP)

(72) Inventor: Noboru Otsushi, Tokyo (JP)

(73) Assignees: ASAHI GROUP FOODS, LTD., Tokyo (JP); ASAHI GROUP HOLDINGS, LTD., Tokyo (JP)

( * ) Notice: Subject to any disclaimer, the term of this patent is extended or adjusted under 35 U.S.C. 154(b) by 1032 days.

(21) Appl. No.: 17/790,718

(22) PCT Filed: Dec. 28, 2020

(86) PCT No.: PCT/JP2020/049073

§ 371 (c)(1),
(2) Date: Jul. 1, 2022

(87) PCT Pub. No.: WO2021/140978

PCT Pub. Date: Jul. 15, 2021

(65) Prior Publication Data

US 2023/0056545 A1 Feb. 23, 2023

(30) Foreign Application Priority Data

Jan. 6, 2020 (JP) ................................ 2020-000189

(51) Int. Cl.
*C12N 9/44* (2006.01)
*A23L 27/00* (2016.01)
*C12N 9/24* (2006.01)

(52) U.S. Cl.
CPC ............ *C12N 9/2405* (2013.01); *A23L 27/84* (2016.08); *A23V 2002/00* (2013.01)

(58) Field of Classification Search
CPC .... C12N 9/2405; A12L 27/84; A23V 2002/00
See application file for complete search history.

(56) References Cited

U.S. PATENT DOCUMENTS

2018/0271130 A1 9/2018 Morel et al.

FOREIGN PATENT DOCUMENTS

| | | | |
|---|---|---|---|
| EP | 3 378 334 | A1 | 9/2018 |
| JP | H04-58893 | A | 2/1992 |
| JP | 2000-037170 | A | 2/2000 |
| JP | 2002-209598 | A | 7/2002 |
| JP | 2018-075043 | A | 5/2018 |
| JP | 2018-531586 | A | 11/2018 |
| JP | 2020-078268 | A | 5/2020 |
| WO | WO-2013/031746 | A1 | 3/2013 |

OTHER PUBLICATIONS

English Translation of JP-2018-531586. Retrieved on May 8, 2025.*
Extended European Search Report issued in corresponding European Patent Application No. 20912163.1, dated Aug. 9, 2023.
International Searching Authority, "International Search Report," issued in connection with International Patent Application No. PCT/JP2020/049073, dated Feb. 2, 2021.
International Searching Authority, "Written Opinion," issued in connection with International Patent Application No. PCT/JP2020/049073, dated Feb. 2, 2021.

* cited by examiner

*Primary Examiner* — Yong D Pak
(74) *Attorney, Agent, or Firm* — Foley & Lardner LLP

(57) ABSTRACT

A composition for improving an unpleasant odor caused by a high-intensity sweetener, such as aspartame, sucrose, acesulfame potassium or stevia, includes an extract of yeast cell walls degraded by a cell wall lytic enzyme such that the degraded extract contains 50 mass % or more of carbohydrates to a dry mass of the degraded extract.

9 Claims, No Drawings

COMPOSITION FOR IMPROVING UNPLEASANT TASTE CAUSED BY HIGH-INTENSITY SWEETENER

CROSS-REFERENCE TO RELATED APPLICATIONS

The present application claims priority under 37 U.S.C. § 371 to International Patent Application No. PCT/JP2020/049073, filed Dec. 28, 2020, which claims priority to and the benefit of Japanese Patent Application No. 2020-000189, filed on Jan. 6, 2020. The contents of these applications are hereby incorporated by reference in their entireties.

TECHNICAL FIELD

The present invention relates to a composition for improving the unpleasant taste caused by high-intensity sweeteners.

BACKGROUND ART

In recent years, food products containing high-intensity sweeteners have become widely known due to diet and health consciousness. As compared to sugar, high-intensity sweeteners have fewer calories, and a strong sweetness can be felt even with small quantities. On the other hand, it has a drawback of having unpleasant tastes such as oral irritation, persistent sweetness and/or harsh taste. Therefore, when developing food products containing high-intensity sweeteners, it is necessary to improve the unpleasant taste caused by high-intensity sweeteners. Among them, methods to improve unpleasant tastes caused by high-intensity sweeteners (masking agents) using yeast extracts, especially yeast essence, have attracted attention (Patent Literature 1 to 3).

CITATION LIST

Patent Literatures

Patent Literature 1: JP 2000-37170 A
Patent Literature 2: WO 2013/031746 A1
Patent Literature 3: JP 2018-75043 A

SUMMARY OF INVENTION

Technical Problem

However, the method disclosed above for improving unpleasant taste caused by high-intensity sweeteners (masking agent) was not satisfactory due to the presence of yeast odor that may cause off-flavor and/or insufficient masking effect of unpleasant taste caused by high-intensity sweeteners.

Therefore, the object of the present invention is to provide a composition capable of improving an unpleasant taste caused by high-intensity sweeteners, in which the yeast odor is improved and/or the masking effect of the unpleasant taste caused by high-intensity sweeteners is sufficiently performed.

Solution to Problem

The present inventors have contemplated upon the above-mentioned problem and after careful examination, they have found that a composition capable of improving an unpleasant taste caused by high-intensity sweeteners, in which the yeast odor is improved and/or the masking effect of the unpleasant taste caused by high-intensity sweeteners is sufficiently performed can be obtained, and thus, have completed the present invention.

Hereinbelow, the present invention provides the following:

[1] a composition for improving the unpleasant taste caused by high-intensity sweeteners, comprising an extract of yeast cell walls degraded by a cell wall lytic enzyme in which the degraded extract contains 50 mass % or more of carbohydrates to the dry mass of the degraded extract;

[2] the composition according to [1], wherein the cell wall lytic enzyme is a glucanase; [3] the composition according to [1] or [2], in which the cell wall lytic enzyme is a glucanase having β-1,3, β-1,4, and/or β-1,6 activity;

[4] the composition according to any of [1] to [3], in which the cell wall lytic enzyme is a glucanase derived from *Streptomyces;*

[5] the composition according to any of [1] to [4], in which the cell wall lytic enzyme is a glucanase not having a protease activity;

[6] the composition according to any of [1] to [5], in which the carbohydrate comprises at least laminarin;

[7] the composition according to any of [1] to [6], in which the degraded extract contains 30 mass % or less of free amino acids and 15 mass % or less of peptides to the dry mass of the degraded extract;

[8] the composition according to any of [2] to [7], in which the degraded extract is obtained from the method comprising:

(a) treating the yeast cell walls with glucanase at 40 to 60° C. and for 1 to 24 hours; and (b) recovering the soluble fraction of the treated product obtained in (a);

[9] the composition according to any of [1] to [8], in which the high-intensity sweeteners are at least one selected from the group consisting of aspartame, sucralose, acesulfame potassium, and stevia;

[10] a method for producing a composition for improving the unpleasant taste caused by high-intensity sweeteners comprising an extract of yeast cell walls degraded by a cell wall lytic enzyme which comprises:

(A) treating yeast cell walls with a cell wall lytic enzyme, and (B) recovering the soluble fraction of the treated product obtained in (A);

[11] a pharmaceutical composition comprising the composition according to any of [1] to [8] and a high-intensity sweetener;

[12] a food composition comprising the composition according to any of [1] to [8] and a high-intensity sweetener;

[13] the food composition according to [12], in which the mass ratio of the high-intensity sweetener contained to the composition according to any of [1] to [8] in the food composition is 1 of the high-intensity sweetener to 0.1 to 10 of the composition according to any of [1] to [8]; and

[14] a method for improving the unpleasant taste caused by the high-intensity sweeteners using the composition according to any of [1] to [8].

Advantageous Effects of Invention

The present invention can provide a composition capable of improving an unpleasant taste caused by high-intensity sweeteners, in which the yeast odor is improved and/or the masking effect of the unpleasant taste caused by high-intensity sweeteners is sufficiently performed.

DESCRIPTION OF EMBODIMENTS

One embodiment of the present invention provides a composition for improving the unpleasant taste caused by high-intensity sweeteners, containing an extract of yeast cell walls degraded by a cell wall lytic enzyme, in which the degraded extract contains 50 mass % or more of carbohydrates to the dry mass of the degraded extract.

Another embodiment of the present invention provides an extract of yeast cell walls degraded by a cell wall lytic enzyme for improving the unpleasant taste caused by high-intensity sweeteners, in which the degraded extract contains 50 mass % or more of carbohydrates to the dry mass of the degraded extract.

Another embodiment of the present invention provides the use of an extract of yeast cell walls degraded by a cell wall lytic enzyme for improving the unpleasant taste caused by high-intensity sweeteners, in which the degraded extract contains 50 mass % or more of carbohydrates to the dry mass of the degraded extract.

Another embodiment of the present invention provides a method for improving the unpleasant taste caused by high-intensity sweeteners comprising orally ingesting an extract of yeast cell walls degraded by a cell wall lytic enzyme, in which the degraded extract contains 50 mass % or more of carbohydrates to the dry mass of the degraded extract.

As used herein, the term "yeast cell walls" is not particularly limited as long as it contains the cell walls of yeast and it may be yeast itself, dried yeast, fungus body residue of the yeast essence, and fractions containing cell wall from these being extracted, or a mixture of these. The term "fungus body residue of the yeast essence" refers to the residue of yeast fungus body after the yeast essence has been extracted. More specifically, it refers to the yeast body produced as residues as a result of known yeast essence extract treatment such as autodigestion treatment (protease treatment), hot water treatment, acid treatment, alkali treatment, and/or mechanical crushing treatment.

Yeasts are not particularly limited as long as they are applicable in the food industry. Examples include yeast for beer production, yeast for bread production, and yeast for sake production. Alternatively, yeasts belonging to the genera *Saccharomyces, Saccharomycodes, Rhodotorula, Endomycopsis, Nematospora, Plethanomyces, Candida, Torulopsis*, and the like, are included, but they are not limited thereto. These may be used alone or in combination of two or more kinds.

As used herein, "a cell wall lytic enzyme" means an enzyme, or combination of enzymes, capable of degrading a part or all of the yeast cell walls. Cell wall lytic enzymes having endo activity are preferred, and those only having endo activity are more preferred. Cell wall lytic enzymes with low, almost no, or no protease activity (i.e., no protease activity) are preferred. Alternatively, when an enzyme with protease activity is used as a cell wall lytic enzyme, or when an enzyme with protease activity coexists, it is preferably used under conditions (e.g., pH, temperature, etc.) where protease activity is suppressed.

Cell wall lytic enzymes, for example, may be derived from natural products, commercially available products, or those obtained by methods using such as genetic recombination technology.

Cell wall lytic enzymes include, for example, such as glucanase and mannanase, but are not limited thereto. Glucanase (preferably having endo activity (preferably only having endo activity), and/or glucanase not having protease activity) is, for example, glucanase having β-1,3, β-1,4, and/or β-1,6 activity, and preferably, glucanase derived from the *Streptomyces* or *Talaromyces*, and more preferably, glucanase derived from *Streptomyces*, and even more preferably, glucanase derived from *Streptomyces* and having β-1,3, β-1,4, and/or β-1,6 glucanase activity, and even more preferably, glucanase derived from *Streptomyces* having β-1,3, β-1,4, and/or β-1,6 activity, and endo activity (preferably only having endo activity), and even more preferably, a glucanase derived from *Streptomyces* having β-1,3, β-1,4, and/or β-1,6 activity, endo activity, and no protease activity (e.g., (such as Denateam GEL1/R manufactured by Nagase Co. Ltd) and even more preferably a glucanase derived from *Streptomyces* having β-1,3, β-1,4, and/or β-1,6 activity, having only endo activity, and no protease activity.

In one embodiment of the present invention, the cell wall lytic enzyme is a glucanase.

In one embodiment of the present invention, the cell wall lytic enzyme is a glucanase having β-1,3, β-1,4, and/or β-1,6 activity.

In one embodiment of the present invention, the cell wall lytic enzyme is a glucanase derived from *Streptomyces*.

In one preferred embodiment of the present invention, the cell wall lytic enzyme is a glucanase derived from *Streptomyces* and having β-1,3, β-1,4, and/or β-1,6 activity.

In one embodiment of the present invention, the cell wall lytic enzyme is a glucanase having endo activity (preferably only having endo activity).

In one preferred embodiment of the present invention, the cell wall lytic enzyme is a glucanase derived from *Streptomyces* having β-1,3, β-1,4, and/or β-1,6 activity and an endo activity (preferably only having endo activity).

In one embodiment of the present invention, the cell wall lytic enzyme is a glucanase not having protease activity.

In one preferred embodiment of the present invention, the cell wall lytic enzyme is a glucanase derived from *Streptomyces*, having β-1,3, β-1,4, and/or β-1,6 activity and an endo activity (preferably only having endo activity), and not having protease activity.

As used herein, "an extract of yeast cell walls degraded by a cell wall lytic enzyme" refers to soluble fraction obtained by degrading the yeast cell walls with a cell wall lytic enzyme.

A method for obtaining "an extract of yeast cell walls degraded by a cell wall lytic enzyme" includes, but not limited to, for example, a known method to a person skilled in the art and the methods disclosed in the Examples, or the following: a method comprising:

(a) treating yeast cell walls with a cell wall lytic enzyme, and (b) recovering the soluble fraction of the obtained treated product, or methods similar thereto.

The "treating" in the above-mentioned (a) is not particularly limited as long as the conditions are such that the cell wall lytic enzyme can degrade the yeast cell walls, and can be changed as appropriate depending on the origin of the yeast cell walls, the kind and/or amount of cell wall lytic enzyme, the desired properties (degree of masking of unpleasant taste by a high-intensity sweeteners, and the like), and the like. The treatment is usually performed in the desired solvent (e.g., water). The treatment is performed, for example, at temperatures from above 0 to about below 100°

C. (preferably from about 10 to 70° C., more preferably from about 25 to 65° C., and even more preferably from about 40 to 60° C.), for about 0.5 to 120 hours (preferably about 0.5 to 60 hours, more preferably about 1 to 24 hours, more preferably about 3 to 24 hours, and even more preferably about 12 to 24 hours), and at pH of about 1 to 12 (preferably about 2 to 10, more preferably about 3 to 8, and even more preferably about 4 to 6).

After the above treatment, the cell wall lytic enzyme may be inactivated by elevated temperature treatment, acid or alkali treatment, etc., if necessary. Alternatively, after the above treatment, the cell wall lytic enzyme may be separated and removed by centrifugation and the like, if necessary.

The recovery of the soluble fraction of the treated product obtained in (a) in the above-mentioned (b) is not particularly limited as long as the method can remove the insoluble fraction and recover the soluble fraction. For example, this includes, under static conditions, centrifugation (e.g., about 100 to 10,000 g), decanting, and the like.

The soluble fraction may be used as "an extract of yeast cell walls degraded by a cell wall lytic enzyme" per se, or if necessary, a further purified form (e.g., HPLC, ultrafiltration, and the like), concentrated form (e.g., air-dried, vacuum filtered, and the like), sterilized form (e.g., heat sterilized, filter sterilized, and the like), dried form (e.g., air-dried, heat, reduced pressure, spray dried, and the like) may be used as "an extract of yeast cell walls degraded by a cell wall lytic enzyme". The conditions for these further processes may be appropriate adjusted by a person skilled in the art.

As used herein, "carbohydrates" include, for example, monosaccharides, disaccharides, trisaccharides, tetrasaccharides, oligosaccharides, polysaccharides, and the like, which may be used alone or in combination of two or more kinds. Examples of carbohydrates include, but are not limited to, ketotriose, aldotriose, erythrulose, ribulose, xylulose, lyxose, deoxyribose, psicose, fructose, sorbose, tagatose, allose, altrose, glucose, mannose, glose, idose, galactose, talose, fucose, fuculose, rhamnose, sedoheptulose, sucrose, lactose, maltose, trehalose, turanose, cellobiose, raffinose, maltotriose, acarbose, stachyose, fructo-oligosaccharides, galacto-oligosaccharides, mannan-oligosaccharides, glycogen, starch, cellulose, dextrin, glucan, laminarin (which is not particularly limited as long as they are disaccharides or more of β-1,3, β-1,6-bound glucose and include laminaribiose, laminaritriose, laminaritetraose, laminaripentaose, laminarihexaose, laminariheptaose, laminarioctaose, laminarinonanaose, and the like), fructan, chitin, and the like, and these may be used alone or in combination of two or more kinds.

The amount of carbohydrate contained in the extract of yeast cell walls degraded by the cell wall lytic enzyme is not particularly limited as long as it is at least 50 mass % or more to the dry mass of the degraded extract, but preferably about 55 mass % or more, and more preferably about 60 mass % or more.

The carbohydrate contained in the extract of yeast cell walls degraded by the cell wall lytic enzyme preferably contains at least laminarin, more preferably contains about 20 mass % or more of laminarin to the total mass of carbohydrates, even more preferably about 30 mass % or more of laminarin to the total mass of carbohydrates, and even more preferably about 50 mass % or more of laminarin to the total mass of the carbohydrates.

In one embodiment of the present invention, the carbohydrate contains at least laminarin.

In one embodiment of the present invention, the carbohydrate contains laminarin of about 50 mass % or more to the total mass of carbohydrates.

As used herein, the term "free amino acid" refers to an amino acid that exists in a free state without forming a peptide by binding with other amino acids. Examples of free amino acids include, but are not limited to, isoleucine, leucine, valine, histidine, lysine, methionine, phenylalanine, threonine, tryptophan, asparagine, aspartic acid, alanine, arginine, cysteine, glutamine, glutamic acid, glycine, proline, serine, and tyrosine. These may be used alone or in a combination of two or more kinds. Free amino acids may be any of L-body, D-body, and DL-body.

The amount of free amino acids contained in the extract of yeast cell walls degraded by the cell wall lytic enzyme is about 30 mass % or less, more preferably about 25 mass % or less, and more preferably about 21 mass % or less to the dry mass of the degraded extract.

In one embodiment of the present invention, the degraded extract contains about 30 mass % or less of free amino acids to the dry mass of the degraded extract.

As used herein, the term "peptide" refers to two or more amino acids bound by a peptide bond, and includes proteins and the like.

The amount of peptides contained in the extract of yeast cell walls degraded by the cell wall lytic enzyme is preferably about 20 mass % or less, more preferably about 15 mass % or less, even more preferably about 12 mass % or less, and even more preferably about 10 mass % or less to the dry mass of the degraded extract.

In one embodiment of the present invention, said degraded extract contains about 20 mass % or less of peptides to the dry mass of the degraded extract.

In one embodiment of the present invention, the degraded extract contains about 30 mass % or less free amino acids and about 15 mass % or less (preferably about 12 mass % or less, more preferably about 10 mass % or less) peptides to the dry mass of the degraded extract.

In one embodiment of the present invention, the degraded extract is obtained from the method comprising:

(a) treating the yeast cell walls with cell wall lytic enzyme (preferably, glucanase) at about 40 to 60° C. and for about 1 to 24 hours; and (b) recovering the soluble fraction of the treated product obtained in (a).

As used herein, the term "high-intensity sweeteners" refers to an artificial or natural sweetener which, with the addition of a small amount, can impart sweetness to food and beverages. High-intensity sweeteners include, but are not limited to, aspartame, sucralose, acesulfame potassium, stevia (rebaudioside, stevioside), somatine, saccharin, sodium saccharin, licorice, Luo han guo, neotame, mabinlin, brazzein, monerin, glycyrrhizin, alitame, cyclamate, zultin, neohesperidin and others, and these can be used alone or in combination of two or more kinds.

In one embodiment of the present invention, the high-intensity sweeteners are at least one selected from the group consisting of aspartame, sucralose, acesulfame potassium and stevia.

As used herein, the term "unpleasant taste caused by high-intensity sweeteners" is not particularly limited as long as it is unpleasant sensation felt when high-intensity sweeteners or a composition containing this (e.g., a food composition (including a beverage), a pharmaceutical composition, and the like) is orally ingested. Unpleasant taste caused by high-intensity sweeteners includes, but are not limited to, for example, oral irritation (e.g., irritation or discomfort felt in the oral cavity or back of the throat), persistent sweetness (e.g., aftertaste, heaviness, and the like), harsh taste, tanic taste, bitterness, astringent taste, and the like.

One embodiment of the present invention provides a method for producing a composition for improving the unpleasant taste caused by high-intensity sweeteners containing an extract of yeast cell walls degraded by the cell wall lytic enzyme which comprises:

(A) treating yeast cell walls with a cell wall lytic enzyme, and (B) recovering the soluble fraction of the treated product obtained in (A).

The treatment in (A) is not particularly limited as long as the conditions are such that the cell wall lytic enzyme can degrade the yeast cell walls, and can be changed as appropriate depending on the origin of the yeast cell walls, the kind and/or amount of cell wall lytic enzyme, the desired properties (degree of masking of unpleasant taste by a high-intensity sweeteners, and the like), and the like. The treatment is generally performed in a desired solvent (e.g., water). The treatment is performed, for example, at temperatures from above 0 to about below 100° C. (preferably from about 10 to about 70° C., more preferably from about 25 to about 65° C., and even more preferably from about 40 to about 60° C.), for about 0.5 to about 120 hours (preferably about 0.5 to about 60 hours, more preferably about 1 to about 24 hours, more preferably about 3 to about 24 hours, and even more preferably about 12 to about 24 hours), and at pH of about 1 to 12 (preferably about 2 to 10, more preferably about 3 to 9, and even more preferably about 4 to 6).

After step (A), the cell wall lytic enzyme may be inactivated by elevated temperature treatment, acid or alkali treatment, and the like, if necessary.

Alternatively, after step (A), the cell wall lytic enzyme may be separated and removed by centrifugation and the like.

The recovery of the soluble fraction of the treated product obtained in (A) in step (B) is not particularly limited as long as the method can remove the insoluble fraction and recover the soluble fraction. For example, this includes, under static conditions, centrifugation (e.g., about 100 to 10,000 g), decanting, and the like.

The soluble fraction recovered by (B) may be used as "an extract of yeast cell walls degraded by the cell wall lytic enzyme" per se, or if necessary, those obtained as a further purified form (e.g., HPLC, ultrafiltration, and the like.), concentrated form (e.g., air-dried, vacuum filtered, and the like), sterilized form (e.g., heat sterilized, filter sterilized, and the like), and dried form (e.g., air-dried, heat, reduced pressure, spray dried, and the like) may be used as "an extract of yeast cell walls degraded by the cell wall lytic enzyme". The conditions for these processes may be appropriate adjusted by a person skilled in the art.

The composition for improving the unpleasant taste caused by high-intensity sweeteners described herein, for example, may be applied to a pharmaceutical composition, a food composition, and the like, which contain or are to contain high-intensity sweeteners or be orally ingested together with the pharmaceutical composition, food composition, and the like, to improve the unpleasant taste caused by high-intensity sweeteners. For example, the composition for improving the unpleasant taste caused by high-intensity sweeteners described herein may be formulated in a pharmaceutical composition, a food composition, and the like, or be mixed with a pharmaceutical composition before medication or with a food composition before, during and/or after cooking.

One embodiment of the present invention provides a pharmaceutical composition comprising a composition for improving the unpleasant taste caused by high-intensity sweeteners described herein and a high-intensity sweetener.

One embodiment of the present invention provides a food composition comprising a composition for improving the unpleasant taste caused by high-intensity sweeteners described herein and a high-intensity sweetener.

The compositions described herein (e.g., pharmaceutical compositions, food compositions) can further contain additives such as, excipients, lubricants, binders, disintegrants, pH adjusters, solvents, solubilizing agents, suspending agents, isotonic agents, buffers, pain relief agents, preservatives, antioxidants, coloring agents, sweetening agents, surfactants, and the like, but are not limited thereto. These additives may use those that are known, for example, and the amount to be used and the like could appropriately be adjusted by a person skilled in the art depending on the purpose.

Pharmaceutical compositions, food compositions, and the like comprising compositions for improving unpleasant taste caused by high-intensity sweeteners described herein, together with the above-mentioned additives, can be formulated by methods known per se, for example, a tablet agent, a coated tablet agent, an orally disintegrating tablet, a chewable agent, a round agent, a granule agent, a fine granule agent, a powder agent, a hard capsule agent, a soft capsule agent, a liquid agent (including, for example, pediatric syrups and the like), a suspension agent, an emulsion agent, and a jelly agent.

Alternatively, a food composition that may apply or include a composition for improving the unpleasant taste caused by high-intensity sweeteners described herein includes juice, confection, swallowing aid jelly, and other processed food that contain or is to contain high-intensity sweeteners, for example, but is not limited thereto.

The adequate amount applied of the composition for improving the unpleasant taste caused by high-intensity sweeteners described herein is not particularly limited as long as the purpose of the present invention can be achieved. Those of the extract of yeast cell walls degraded by the cell wall lytic enzyme (dry mass) to the total amount of a pharmaceutical composition, a food composition, and the like, or the formulation of these, for example, can be about 0.00001 to 10 mass %, preferably about 0.0001 to 5 mass %, more preferably about 0.001 to 3 mass %, and further preferably about 0.01 to 1 mass %. Alternatively, the mass ratio of the high-intensity sweetener to the extract of yeast cell walls degraded by the cell wall lytic enzyme (dry mass) that are contained or are to be contained in a pharmaceutical composition, a food composition, and the like, or the formulation of these, for example, can be, 1 of the high-intensity sweetener to about 0.00001 to 1, preferably about 0.0001 to 0.1, more preferably about 0.001 to 0.01, further preferably about 0.0001 to 0.1, and even more preferably about 0.001 to 0.01 of the extract of yeast cell walls degraded by the cell wall lytic enzyme (dry mass). Alternatively, the mass ratio of the high-intensity sweetener to the extract of yeast cell walls degraded by the cell wall lytic enzyme (dry mass) that are contained or are to be contained in a pharmaceutical composition, a food composition, and the like, or the formulation of these, for example, can be, "1 high-intensity sweetener/sweetness level of the high-intensity sweetener" to about 0.00001 to 1, preferably about 0.0001 to 0.1, more preferably about 0.001 to 0.01 of the extract of yeast cell walls degraded by the cell wall lytic enzyme (dry mass). As used herein, the term "sweetness level" refers to the sweetness of a high-intensity sweetener when the level of sugar is defined as 1.

One embodiment of the present invention provides a pharmaceutical composition in which the mass ratio of the high-intensity sweetener to a composition for improving the unpleasant taste caused by high-intensity sweeteners described herein included in the pharmaceutical composition is 1 of the high-intensity sweetener to about 0.1 to 10 of the composition for improving the unpleasant taste caused by high-intensity sweeteners described herein.

One embodiment of the present invention provides a food composition in which the mass ratio of the high-intensity sweetener to a composition for improving the unpleasant taste caused by high-intensity sweeteners described herein included in the food composition is 1 of the high-intensity sweetener to about 0.1 to 10 of the composition for improving the unpleasant taste caused by high-intensity sweeteners described herein.

Another embodiment of the present invention provides a method for improving the unpleasant taste caused by high-intensity sweeteners used in the composition described herein.

EXAMPLES

Hereinbelow, the invention will be described in more detail below using Examples, but these Examples are not in any way limiting the scope of the invention.

Example 1

A suspension (16% in water) of dried yeast (manufactured by Asahi Group Foods Corporation, Hyper Yeast HG-DY) was sterilized in an autoclave (121° C., 20 min). To the sterilized suspension, under conditions of 50° C. and pH 5.5, 0.5 mass % of glucanase to the dry mass of the dried yeast (manufactured by Nagase Sangyo Co., Denateam GEL1/R) was added and treated at 50° C. for 20 hours. The treated product was then brought to about 80° C. to inactivate glucanase, and the supernatant (soluble fraction) was obtained by centrifugation (5000 g, 5 min). The supernatant was concentrated, and spray dried to obtain the composition of Example 1.

Comparative Example 1

Hot water extract essence of dried yeast (manufactured by Asahi Group Foods, Ltd., HYPER MEAST HG-Ps) was used as the composition of Comparative Example 1. Here, the composition of Comparative Example 1 was made by extracting dried yeast (manufactured by Asahi Group Foods, Ltd., Hyper Yeast HG-DY) with hot water, centrifuging this, concentrating the obtained supernatant, and spray drying the same.

Comparative Example 2

Autolytic yeast essence (manufactured by Asahi Group Foods, Ltd., Yeastock Yeast Pepton S-Ps) was made into the composition of Comparative Example 2.

Example 2

As fungus body residue of the yeast essence, dried product of hot water extract residue obtained when preparing hot water extract essence of dried yeast (manufactured by Asahi Group Foods, Ltd., HYPER MEAST HG-Ps) of Comparative Example 1 was used. A suspension (16% in water) of fungus body residue of the yeast essence was sterilized in an autoclave (121° C., 20 min). To the sterilized suspension, under conditions of 50° C. and pH 5.5, 0.5 mass % of glucanase to the dry mass of fungus body residue of the yeast essence (manufactured by Nagase Sangyo Co., Denateam GEL1/R) was added and treated at 50° C. for 20 hours. The treated product was then brought to about 80° C. to inactivate glucanase, and the supernatant (soluble fraction) was obtained by centrifugation (5000 g, 5 min). The supernatant was concentrated up to 40% and spray dried to obtain the composition of Example 2.

Example 3

A suspension (16% in water) of the fungus body residue of the yeast essence of Example 2 was sterilized in an autoclave (121° C., 20 min). To the sterilized suspension, 0.2 mass % of enzyme protease (manufactured by Novozyme Japan Co. Ltd., Alcalase (registered trademark) 2.4 L FG) to the dry mass of the fungus body residue of the yeast essence under the conditions of 60° C. and pH 8 was added, and the enzymatic degradation treatment was conducted at 60° C. for 20 hours. The treated product was then brought to about 90° C. to inactivate protease, and the supernatant (soluble fraction) was removed by centrifugation (5000 g, 5 min), the insoluble fraction containing yeast cell walls was recovered and spray dried to obtain the second fungus body residue of the yeast essence.

A suspension (14% in water) of this obtained second fungus body residue of the yeast essence was sterilized in an autoclave (121° C., 20 min). To the sterilized suspension, under conditions of 50° C. and pH 5.5, 0.5 mass % of glucanase to the dry mass of the second fungus body residue of the yeast essence (manufactured by Nagase Sangyo Co., Denateam GEL1/R) was added and treated at 50° C. for 20 hours. The treated product was then brought to about 80° C. to inactivate glucanase, and the supernatant (soluble fraction) was obtained by centrifugation (5000 g, 5 min). The supernatant was concentrated up to 40% and spray dried to obtain the composition of Example 3.

Test Example 1: Sensory Evaluation Using Aspartame

The following sensory tests were conducted on five panelists.

0.05 mass % of aspartame (manufactured by Ajinomoto Co., Ltd.) aqueous solution (hereinafter, referred to as "only Aspartame") was orally ingested, and the yeast odor, oral irritation, persistent sweetness, harsh taste, sugar-like taste quality, and umami taste perceived by each person at the moment were rated as "0" for each person. Then, to a 0.05 mass % of aspartame aqueous solution, the composition of Examples 1, 2, or 3 or the composition of Comparative Example 1 or 2 were added so that the final concentration would be 0.05 mass %, this was orally ingested, and the yeast odor, oral irritation, persistent sweetness, harsh taste, sugar-like taste quality, and umami taste perceived by each person at the moment were evaluated within the range of −3 to +3 (i.e., in the range of −3, −2, −1, 0, 1, 2, and 3) with the above-mentioned "0" as a standard. A negative value (i.e., <0) means that the target endpoint was "weaker, less, or not persistent" compared to the "only aspartame" endpoint, and a positive value (i.e., >0) means that the target endpoint was "stronger, more, or persistent" as compared to the "only aspartame" endpoint.

The results of the calculation of the average values of the values obtained in each end point are shown below in Tables 1 and 2.

Note that the "yeast odor" preferably is a negative value (the yeast odor is weaker as compared to that of "only aspartame"); "oral irritation sensation" preferably is a negative value (the oral irritation sensation is weaker as compared to that of "only aspartame"); "persistent sweetness" preferably is a negative value (the sweetness does not persist as compared to that of "only aspartame", i.e., the unique sweetness of aspartame is likely to disappear); "harsh taste" preferably is a negative value ("harsh taste" is weaker as compared to that of "only aspartame"); "sugar-like taste quality" is preferably a positive value (sugar-like taste quality is stronger as compared to that of "only aspartame"); "umami taste is preferably 0 or a negative value (umami taste is the same level or weaker as compared to that of "only aspartame", i.e., no unnecessary umami taste is added).

TABLE 1

| | Only aspartame | Example 1 | Comparative Example 1 | Comparative Example 2 |
|---|---|---|---|---|
| Yeast odor | 0.0 | 0.0 | 1.8 | 2.6 |
| Oral irritation sensation | 0.0 | −2.4 | −0.8 | −0.4 |
| Persistent sweetness | 0.0 | −2.2 | −1.2 | −0.8 |
| Harsh taste | 0.0 | −2.0 | −0.8 | −0.8 |
| Sugar-like taste quality | 0.0 | 1.6 | −0.2 | −2.0 |
| Umami taste | 0.0 | 0.0 | 2.2 | 1.6 |

TABLE 2

| | Only aspartame | Example 2 | Example 3 |
|---|---|---|---|
| Yeast odor | 0.0 | −2.2 | −1.8 |
| Oral irritation sensation | 0.0 | −2.0 | −1.2 |
| Persistent sweetness | 0.0 | −2.0 | −1.0 |
| Harsh taste | 0.0 | 1.6 | 0.8 |
| Sugar-like taste quality | 0.0 | 0.0 | 0.0 |
| Umami taste | 0.0 | 0.0 | 0.0 |

Test Example 2: Sensory Evaluation Using Sucralose

The sensory tests by the same method as Test Example 1 were conducted on five panelists.

In Test Example 2, instead of 0.05 mass % of aspartame aqueous solution, 0.015 mass % of sucralose (manufactured by San-Ei Gen F.F.I Co., Ltd.) aqueous solution was used.

The results are shown below in Tables 3 and 4.

TABLE 3

| | Only sucralose | Example 1 |
|---|---|---|
| Yeast odor | 0.0 | 0.0 |
| Oral irritation sensation | 0.0 | −1.8 |
| Persistent sweetness | 0.0 | −1.8 |
| Harsh taste | 0.0 | −1.8 |
| Sugar-like taste quality | 0.0 | 1.2 |
| Umami taste | 0.0 | 0.0 |

TABLE 4

| | Only sucralose | Example 2 | Example 3 |
|---|---|---|---|
| Yeast odor | 0.0 | −2.2 | −1.2 |
| Oral irritation sensation | 0.0 | −1.8 | −1.6 |
| Persistent sweetness | 0.0 | −2.0 | −1.6 |
| Harsh taste | 0.0 | 1.6 | 0.8 |
| Sugar-like taste quality | 0.0 | 0.0 | 0.0 |
| Umami taste | 0.0 | 0.0 | 0.0 |

Test Example 3: Sensory Evaluation Using Acesulfame Potassium

The sensory tests by the same method as Test Example 1 were conducted on five panelists.

In Test Example 3, instead of 0.05 mass % of aspartame aqueous solution, 0.05 mass % of acesulfame potassium (manufactured by San-Ei Gen F.F.I Co., Ltd.) aqueous solution was used.

The results are shown below in Tables 5 and 6.

TABLE 5

| | Only acesulfame potassium | Example 1 |
|---|---|---|
| Yeast odor | 0.0 | 0.0 |
| Oral irritation sensation | 0.0 | −1.6 |
| Persistent sweetness | 0.0 | −1.6 |
| Harsh taste | 0.0 | −1.6 |
| Sugar-like taste quality | 0.0 | 1.0 |
| Umami taste | 0.0 | 0.0 |

TABLE 6

| | Only acesulfame potassium | Example 2 | Example 3 |
|---|---|---|---|
| Yeast odor | 0.0 | −1.4 | −1.4 |
| Oral irritation sensation | 0.0 | −1.2 | −2.0 |
| Persistent sweetness | 0.0 | −2.2 | −1.6 |
| Harsh taste | 0.0 | 0.8 | 0.4 |
| Sugar-like taste quality | 0.0 | 0.0 | 0.0 |
| Umami taste | 0.0 | 0.0 | 0.0 |

Test Example 4: Sensory Evaluation Using *Stevia*

The sensory tests by the same method as Test Example 1 were conducted on five panelists.

In Test Example 4, instead of 0.05 mass % of aspartame aqueous solution, 0.03 mass % of stevia (manufactured by Morita Kagaku Kogyo Co., Ltd.) aqueous solution was used.

The results are shown below in Tables 7 and 8.

TABLE 7

| | Only stevia | Example 1 |
|---|---|---|
| Yeast odor | 0.0 | 0.0 |
| Oral irritation sensation | 0.0 | −2.4 |
| Persistent sweetness | 0.0 | −2.2 |
| Harsh taste | 0.0 | −2.4 |
| Sugar-like taste quality | 0.0 | 1.4 |
| Umami taste | 0.0 | 0.0 |

TABLE 8

| | Only stevia | Example 2 | Example 3 |
|---|---|---|---|
| Yeast odor | 0.0 | −2.2 | −2.2 |
| Oral irritation sensation | 0.0 | −2.4 | −1.8 |
| Persistent sweetness | 0.0 | −2.4 | −1.8 |
| Harsh taste | 0.0 | 1.6 | 1.0 |
| Sugar-like taste quality | 0.0 | 0.0 | 0.0 |
| Umami taste | 0.0 | 0.0 | 0.0 |

Test Example 5: Composition Analysis

The composition of each component contained in the compositions of Examples 1 to 3 and Comparative Examples 1 and 2 was analyzed. The results are shown below in Tables 9 and 10. The analytical method for each component and the calculation method for the content ratio of each component are as follows. Note that unless otherwise stated, content means mass %.

<Proteins>

Protein was measured by the combustion method (modified Dumas method) and calculated as percentage (%) to the dry mass of each composition. The protein content (%) calculated by such a method is the total amount of free amino acids and peptides.

<Free Amino Acids>

The content (%) of free amino acids contained in the dry mass of each composition was determined by a pre-derivatized LC-PDA method (manufactured by Waters Corporation).

Analytical Device: Ultra Performance LC (UPLC®) (manufactured by Waters Corporation)

Detectors: Photodiode array (PDA) (manufactured by Waters Corporation)

Column: AccQ-Tag Ultra RP Column (130 Å, 1.7 μm, 2.1 mm×100 mm, manufactured by Waters Corporation)

Column temperature: 55° C.

Sample temperature: 10° C.

Mobile phase: AccQ-Tag Ultra Eluent A (manufactured by Waters Corporation) as liquid A and AccQ-Tag Ultra Eluent B (manufactured by Waters Corporation) as liquid B <Peptide>

The peptide content (%) in the dry mass of each composition was calculated by subtracting the free amino acid content (%) calculated above from the protein content (%) calculated above.

<Carbohydrates>

The carbohydrate content (%) in the dry mass of each composition was calculated using the following formula.

$$\text{the Carbohydrate Content } (\%) = 100 - (A + B + C + D)$$

A: Protein content measured by the combustion method (modified Dumas method) (%)

B: Water content measured by the atmospheric pressure thermal drying method (%)

C: Lipid content measured by acid degradation method (%)

D: Ash content measured by direct ashing method (%)

<Laminarin>

Percentage (%) of laminarin to the total mass of carbohydrates was calculated based on the content (%) of each ingredient contained in the compositions of Example 1 and Comparative Example 1.

* The compositions of Examples 1 to 3 differ from the composition of Comparative Example 1 in that they contain an extract of yeast cell walls degraded by a cell wall lytic enzyme, and the extract is considered to be mostly or almost entirely carbohydrate. Accordingly, the compositions of Examples 1 to 3 were estimated to have mostly only or only relative increase of carbohydrates (i.e., there are hardly any or no increase for the other components, resulting in a relative decrease) compared to the composition of Comparative Example 1, and based on this, percentage of laminarin (%) was calculated.

<Glucose>

Percentage (%) of glucose to the total mass of carbohydrates was determined by enzyme catalysis reaction and hydrogen peroxide electrode detection method (using equipment manufactured by Oji Scientific Instruments Co., Ltd.).

TABLE 9

| | Example 1 | Comparative Example 1 | Comparative Example 2 |
|---|---|---|---|
| His (%) | 0.06 | 0.07 | 0.24 |
| Asn (%) | 0.13 | 0.16 | 1.14 |
| Ser (%) | 0.21 | 0.29 | 1.33 |
| Gln (%) | 0.01 | 0.00 | 0.00 |
| Arg (%) | 0.10 | 0.09 | 1.12 |
| Gly (%) | 0.49 | 0.65 | 0.64 |
| Asp (%) | 0.90 | 1.36 | 2.22 |
| Glu (%) | 14.90 | 25.05 | 2.35 |
| Thr (%) | 0.06 | 0.07 | 1.35 |
| Ala (%) | 1.63 | 2.36 | 3.09 |
| Pro (%) | 0.68 | 1.58 | 2.66 |
| Cys (%) | 0.00 | 0.00 | 0.22 |
| Lys (%) | 0.12 | 0.19 | 1.39 |
| Tyr (%) | 0.30 | 0.30 | 1.33 |
| Met (%) | 0.02 | 0.00 | 0.72 |
| Val (%) | 0.29 | 0.37 | 2.54 |
| Ile (%) | 0.29 | 0.32 | 2.08 |
| Leu (%) | 0.25 | 0.26 | 3.27 |
| Phe (%) | 0.16 | 0.15 | 1.85 |
| Trp (%) | 0.03 | 0.15 | 0.45 |
| Total free amino acids (%) | 20.63 | 33.44 | 30.01 |
| Proteins (%) | 29.10 | 46.20 | 74.40 |
| Peptides (%) | 8.47 | 12.76 | 44.39 |
| Carbohydrates (%) | 63.10 | 44.90 | 11.20 |
| Percentage (%) of laminarin to the total mass of carbohydrates | ≥50 | trace amount | trace amount |
| Percentage (%) of glucose to the total mass of carbohydrates | 0.48% | 0.22% | trace amount |

TABLE 10

| | Example 2 | Example 3 |
|---|---|---|
| Total free amino acids (%) | 8.28 | 5.32 |
| Proteins (%) | 16.51 | 16.68 |
| Peptides (%) | 8.23 | 11.36 |
| Carbohydrates (%) | 79.38 | 79.92 |
| Percentage (%) of laminarin to the total mass of carbohydrates | ≥50 | ≥50 |
| Percentage (%) of glucose to the total mass of carbohydrates | trace amount | trace amount |

RESULTS

The results of Test Example 1 show that the compositions of Examples 1 to 3 as compared to the compositions of Comparative Examples 1 and 2, have significantly improved the yeast odor and the unpleasant taste caused by aspartame, such as oral irritation, persistent sweetness, and harsh taste. Furthermore, it was revealed that the composition of Example 1 has a stronger sugar-like taste quality than the compositions of Comparative Examples 1 and 2, and does not have an added unnecessary umami taste.

The results of Test Examples 2 to 4 show that the compositions in Examples 1 to 3 demonstrate the above-mentioned effect, not only to aspartame but also to a variety of high-intensity sweeteners.

The results of Test Example 5 revealed that the composition of Example 1 contains about 21 mass % of total free amino acids, about 8 mass % of peptides, and about 63 mass % of carbohydrates. On the other hand, it was revealed that the compositions of Comparative Examples 1 and 2 contain more than 30 mass % of total free amino acids, about 12 mass % of peptides, and less than 50 mass % of carbohydrates. Thus, the compositions described herein are considered to exhibit the effects described above when carbohydrates (preferably carbohydrates containing at least laminarin) are 50 mass % or more (more preferably when carbohydrates are 50 mass % or more, free amino acids are about 30 mass % or less, and peptides are about 12 mass % or less). Moreover, as compared to the composition of the Comparative Example 1, the composition of Example 1 is revealed to have less glutamic acid which is considered to be an umami component. Therefore, it is possible that the composition of Example 1 improves the unpleasant taste caused by high-intensity sweeteners without depending on the content of umami components derived from amino acids such as glutamic acid.

As shown above in the Examples, the present invention can provide a composition capable of improving an unpleasant taste caused by high-intensity sweeteners, in which the yeast odor is improved and/or the masking effect of the unpleasant taste caused by high-intensity sweeteners is sufficiently performed.

The invention claimed is:

1. A composition comprising an extract of yeast cell walls degraded by glucanase, wherein the degraded extract contains 50 mass % or more of carbohydrates to a dry mass of the degraded extract and the carbohydrates comprise 50 mass % or more of laminarin to a total mass of the carbohydrates.

2. The composition according to claim 1, wherein the glucanase is a glucanase having β-1,3, β-1,4, and/or β-1,6 activity.

3. The composition according to claim 1, wherein the glucanase is a glucanase derived from *Streptomyces*.

4. The composition according to claim 1, wherein the glucanase is a glucanase not having a protease activity.

5. The composition according to claim 1, wherein the degraded extract contains 30 mass % or less of free amino acids and 15 mass % or less of peptides to the dry mass of the degraded extract.

6. The composition according to claim 1, wherein the degraded extract is obtained from the method comprising:

(A) treating the yeast cell walls with the glucanase at 40 to 60° C. and for 1 to 24 hours; and (B) recovering the soluble fraction of the treated product obtained in (A).

7. A pharmaceutical composition comprising the composition according to claim 1 and a sweetener selected from the group consisting of aspartame, sucralose, acesulfame potassium and stevia.

8. A food composition comprising the composition according to claim 1 and a sweetener selected from the group consisting of aspartame, sucralose, acesulfame potassium and stevia.

9. The food composition according to claim 8, wherein the mass ratio of the sweetener to the composition contained in the food composition is 1 of the sweetener to 0.1 to 10 of the composition.

* * * * *